United States Patent
Feiweier et al.

(10) Patent No.: US 8,548,217 B2
(45) Date of Patent: Oct. 1, 2013

(54) METHOD AND MAGNETIC RESONANCE SYSTEM TO CORRECT DISTORTIONS IN IMAGE DATA

(75) Inventors: Thorsten Feiweier, Poxdorf (DE); Stefan Huwer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 569 days.

(21) Appl. No.: 12/874,592

(22) Filed: Sep. 2, 2010

(65) Prior Publication Data

US 2011/0052031 A1 Mar. 3, 2011

(30) Foreign Application Priority Data

Sep. 2, 2009 (DE) .......................... 10 2009 039 772

(51) Int. Cl.
*G06K 9/00* (2006.01)
(52) U.S. Cl.
USPC .......................................................... 382/131
(58) Field of Classification Search
None
See application file for complete search history.

(56) References Cited

U.S. PATENT DOCUMENTS

| | | | |
|---|---|---|---|
| 6,788,062 B2 | 9/2004 | Schweikard et al. | |
| 6,969,991 B2 * | 11/2005 | Bammer et al. | 324/307 |
| 7,034,531 B1 * | 4/2006 | Tuch et al. | 324/309 |
| 7,902,825 B2 * | 3/2011 | Bammer et al. | 324/309 |
| 2004/0113615 A1 | 6/2004 | Bammer et al. | |
| 2009/0022384 A1 | 1/2009 | Ritter | |

OTHER PUBLICATIONS

"Eddy Current Correction in Diffusion-Weighted Imaging Using Pairs of Images Acquired With Opposite Diffusion Gradient Polarity," Bodammer et al., Magnetic Resonance in Medicine, vol. 51 (2004) pp. 188-193.

"Correction for Distortion of Echo-Planar Images Used to Calculate the Apparent Diffusion Coefficient," Haselgrove et al., Magnetic Resonance in Medicine, vol. 36 (1996) pp. 960-964.

"Correction of Eddy-Current Distortions in Diffusion Tensor Images Using the Known Directions and Strengths of Diffusion Gradients," Zhuang et al., Journal of Magnetic Resonance Imaging, vol. 24, (2006) pp. 1188-1193.

\* cited by examiner

*Primary Examiner* — Claire X Wang
(74) *Attorney, Agent, or Firm* — Schiff Hardin LLP (57) ABSTRACT

In a method for correction of distortions in image data in a diffusion imaging, the image data are acquired with an imaging MRT measurement for a predetermined diffusion weighting and map a predetermined image segment. A diffusion model for the image segment is determined. Output image data are determined for the image segment such that the output image data are essentially free of distortions caused by diffusion weighting. Reference image data are estimated for the predetermined diffusion weighting for the image segment based on the output image data and the diffusion model. The acquired image data are compared with the reference image data and the acquired image data are corrected based on the comparison.

22 Claims, 5 Drawing Sheets

METHOD AND MAGNETIC RESONANCE SYSTEM TO CORRECT DISTORTIONS IN IMAGE DATA

BACKGROUND OF THE INVENTION

1. Field of the Invention

The present invention concerns a method to correct distortions in image data in a diffusion imaging, and a magnetic resonance system for this purpose. The invention in particular concerns the correction of distortions in the image data that depend on a diffusion weighting and/or diffusion direction in the acquisition of the image data.

2. Description of the Prior Art

Diffusion-weighted magnetic resonance (MR) image data can provide diagnostic information that is important in the clinical routine, for example in stroke and tumor diagnostics. In diffusion-weighted imaging (DWI), diffusion gradients are switched (activated) in specific directions, and the diffusion of water molecules along the applied diffusion gradients attenuates the measured magnetic resonance signal. In areas with lower diffusion, a lesser signal attenuation therefore occurs, such that these regions are imaged with higher image intensity in an imaging magnetic resonance tomography (MRT) measurement. The strength of the diffusion weighting is thereby correlated with the strength of the applied diffusion gradients. The diffusion weighting can be characterized with what is known as the b-value, which is a function of gradient parameters (for example the gradient strength, duration or the interval between the applied diffusion gradients). The acquisition of the resulting magnetic resonance signals ensues with a readout sequence, for example an echoplanar imaging sequence (EPI).

It is essentially the signal-to-noise ratio (SNR) and geometric distortions that are significant for the quality of acquired, diffusion-weighted image data. The time sequence of the switched diffusion gradient pulses can thereby cause dynamic distortions, for example due to eddy current effects. Every activation and deactivation of field gradients can induce such eddy currents, which partially decay with relatively long time constants. Upon readout—i.e. upon measurement of the magnetic resonance signals—corresponding field portions can remain, such that distortions result in the acquired image data. In particular in diffusion-weighted EPI imaging, distortions due to eddy currents represent a significant challenge since here high gradient amplitudes are used in combination with a high sensitivity (for example approximately 10 Hz/image element in the phase coding direction in EPI imaging).

In diffusion imaging, multiple images with different diffusion directions and weightings (characterized by the b-value) are normally acquired and combined with one another in order to calculate parameter maps (Apparent Diffusion Coefficient ADC, Fractional Anisotropy FA), for example. The image distortions caused by the diffusion gradients thereby depend both on the amplitude of the gradients (diffusion weighting) and on their direction (diffusion gradient direction). Given a combination of corresponding individual images, the different distortions for each image lead to incorrect associations of image element information, and therefore to errors or at least to a reduced precision in the calculation of parameters. The distortions can be described as simple affine transformations. The problem is thus created to determine the corresponding transformations to compensate for these distortions. The determination is hindered in that—among other things—the image contrast changes with the varying diffusion weightings and diffusion gradient directions.

To reduce the distortions, the method described in Haselgrove et al., MRM 36:960, 1996 is known in which a b=0 image is acquired as an undistorted reference and an additional image is acquired with a slight diffusion weighting (for example b=150 s/mm$^2$) for every direction to be corrected. Assuming that the distortion effects scale linearly with the amplitude of the generated diffusion gradients, the distortion parameters are thereby determined using an extrapolation. The actual diffusion-weighted images are corrected with this (for example b=1000 s/mm$^2$). However, in this method an adjustment measurement is necessary for every diffusion gradient direction. The determination of the distortion parameters ensues via registration of the image data of the adjustment measurement and the reference measurement. However, the corresponding image data possess only a similar—not identical—contrast, which leads to a lacking robustness of the method, in particular if tissue with rapidly diffusing water molecules (for example spinal fluid or eyeballs) is present in the mapped image segment. Errors in the registration of the image with slight diffusion weighting are furthermore intensified by the extrapolation. In these slightly weighted images distortion are also not strongly expressed, such that a precise determination of the distortion parameters is difficult, wherein errors are again intensified by the extrapolation. A movement of the imaged subject between the acquisition of the reference and the adjustment measurement can lead to an incorrect determination of the correction parameters.

Furthermore, from the printed document Bodammer et al., MRM 51:188-193, 2004 a method is known in which two respective images with identical diffusion direction and diffusion weighting but inverted polarity of the diffusion gradients (i.e. opposite diffusion gradient directions) are acquired. The inverted polarity leads to an unmodified diffusion contrast with a simultaneous inversion of the distortions (a compression is made from a stretching, for example). Due to the identical contrast the registration of the images is facilitated; an extrapolation is also unnecessary. However, two images must respectively be acquired for each diffusion direction and for each diffusion weighting. Given high b-values (diffusion weightings), the signal-to-noise ratio (SNR) in the acquired image data can be very low, such that the registration of the image data and the determination of the distortion parameters is difficult and plagued with a greater imprecision. Furthermore, contrast differences due to directed movement—for example flow or polarization—can lead to a lacking robustness of the method. Movements of the imaged subject between the acquisition of the two measurements can moreover lead to an incorrect determination of the correction parameters.

SUMMARY OF THE INVENTION

An object of the present invention is to enable an improved correction of distortions in diffusion-weighted image data, and at least to avoid some of the aforementioned disadvantages.

According to a first aspect of the present invention, a method is provided for the correction of distortions in image data in a diffusion imaging, wherein the image data were acquired with an imaging magnetic resonance tomography (MRT) measurement for a predetermined diffusion weighting and map a predetermined image segment. The method includes the determination of a diffusion model for the image segment; the determination of output image data for the image segment such that the output image data are essentially free of distortions caused by diffusion weighting; the estimation of reference image data for the predetermined diffusion weighting for the image segment based on the output image data and the diffusion model; the comparison of the acquired image data with the reference image data; and the correction of the acquired image data based on the comparison.

In particular, distortions can thus be corrected that depend on the diffusion direction and/or the diffusion weighting. The output image data can be determined such that they correspond to image data that were acquired in an MRT measurement that was not diffusion-weighted. By applying the diffusion model to these output image data it is thus possible to estimate an undistorted reference image for the predetermined diffusion weighting. In particular, the reference image data can be estimated for the same predetermined diffusion weighting such that they exhibit essentially the same image contrast as the acquired image data. The reference image data can also exhibit a high signal-to-noise ratio (SNR). A precise comparison of the acquired image data with the reference image data is thus enabled without having to take contrast variations into account. A more precise determination of the distortions that can therefore be achieved enables an improved correction of the acquired image data. In the method it is also not necessary to acquire additional reference images or adjustment images for an acquired image to be corrected. A reference image can be estimated for any image acquired with arbitrary diffusion weighting, without additional measurements.

According to one embodiment of the method according to the invention, in the comparison a transformation between the acquired image data and the reference image data is determined, wherein the correction of the acquired image data comprises the application of the transformation to the acquired image data. For example, the comparison can be an affine registration of the acquired image data with the reference image data (as a registration goal) to determine a transformation between these. Since no extrapolation is necessary and the distortions in the acquired image data can already be significantly developed, a precise determination of the transformation is possible. The transformation can include at least one scaling (M), a shearing (S) or a displacement (shifting) (T), or a combination of these. A precise determination of these distortion parameters is possible by means of the image registration of the acquired image data with the reference image data. A precise and robust image registration can be implemented due to the similarity of the contrast of the reference image data and the acquired image data.

Furthermore, the reference image data can be estimated for the same diffusion direction for which the image data were acquired. The diffusion direction that is imaged in the acquisition of the image data can thereby be determined via the direction of the applied diffusion coding gradient (diffusion gradient direction). The consideration of the diffusion direction enables a more precise estimation of the reference image data since regions of the imaged subject can exhibit different diffusion coefficients for different directions, for example due to a structuring of the imaged subject (for example due to muscle fibers, nerve tracts or the like).

In one embodiment of the method according to the invention, the diffusion model can comprise a diffusion tensor for every image element in the image segment. An image element can, for example, be a pixel (two-dimensional imaging) or a voxel (three-dimensional imaging). For a voxel the diffusion can be described by a diffusion tensor of the 2nd order, for example. Such a tensor includes six unknowns that can be determined in the determination of the diffusion model.

The diffusion model can also comprise a HARDI (High Angular Resolution Diffusion Imaging), a kurtosis model, a QBall model or a multi-tensor model. Such models enable a precise description of diffusion processes within a region (for example a volume region such as a voxel) and can possibly also take sub-structures into account.

The diffusion model can describe a change of an intensity in the image data with the diffusion weighting and diffusion direction, wherein the estimation of the reference image data can ensue in that the diffusion model for the diffusion weighting and diffusion direction with which the image data to be corrected were acquired is applied to the output image data. The diffusion model can thus describe the attenuation of a magnetic resonance (MR) signal with different diffusion weightings and diffusion directions. The signal attenuation corresponds to an intensity change of the corresponding image elements in the image data. The diffusion model moreover depends on the diffusion coefficients for the corresponding diffusion direction (which diffusion coefficients are significant for the image element) that, for example, can be described by the aforementioned diffusion tensor.

According to one embodiment, the method furthermore includes the acquisition of multiple image data sets for different diffusion directions given the same or different diffusion weightings, as well as the determination of the diffusion model on the basis of the acquired image data sets. Parameters of the diffusion model can thus be determined, for example the components of the aforementioned diffusion tensor D, wherein image data sets for at least six different diffusion directions can be acquired to determine six unknown tensor components. These can be acquired with different or the same diffusion weightings. Naturally, more image data sets can also be acquired in order to further increase the precision of the determination of the diffusion model.

The method of least squares can be used to adapt the diffusion model to the acquired image data sets. For example, for every pixel of the image segment a corresponding diffusion tensor can be determined so that the intensity changes described by the diffusion model deviate only slightly from the actual changes of the intensity in the acquired image data sets.

An image data set represents image data for a specific diffusion direction and diffusion weighting.

An analysis of the multiple acquired image data sets for image interference (distortion) can ensue. If an image interference is present, a correction of the image interference can ensue in the corresponding image data set, or the corresponding image data set can be excluded from use in determining the diffusion model. Image interference can thereby be artifacts or rigid movements of the examination subject, for example. It is also possible to remeasure the corresponding image data set. Furthermore, methods increasing SNR can be applied.

The diffusion gradient $g_i$ and diffusion weightings $b_i$ can be selected in the acquisition of the image data sets for the determination of the diffusion model such that the sum of the diffusion gradient direction weighted with the respective diffusion weighting essentially yields a null vector. If the image data sets are acquired under such conditions, it is enabled that distortions in the acquired image data sets average out in the determination of the diffusion model. Such an overlaying can allow the eddy current effects to essentially disappear. Moreover, it can thus be ensured that the determined diffusion model—for example the diffusion tensor—does not exhibit any bias or, respectively, alignment in a specific direction. The condition can thereby also be designated as a "white distribution" of the diffusion weightings and diffusion directions.

For example, at least six image data sets can be acquired for different diffusion gradient directions and six image data sets can be acquired with respective opposite diffusion gradient direction given the respective same diffusion weighting. The polarity of the diffusion gradients can thus be inverted in the acquisition of the image data sets. A particularly efficient compensation of the distortions that are induced by the diffusion coding is therefore achieved in the determination of the diffusion model.

One of the image data sets can moreover be acquired without diffusion weighting (i.e. b=0). This image data set can serve to determine the output image data or as a control.

The acquisition of at least a portion of the multiple image data sets can ensue within an adjustment measurement that is implemented before an acquisition of the image data to be corrected. The image data sets can thus be acquired with freely selectable diffusion directions and weightings, and the determination of a diffusion model is enabled before the acquisition of the image data to be corrected. However, the image data sets to determine the diffusion can also be acquired as part of a diffusion measurement. In particular the diffusion model can be determined under consideration of the acquired image data to be corrected. An inline concurrent measurement is thus enabled and the diffusion model can be successively improved since more data to determine the diffusion model are provided with the progression of the diffusion measurement.

A diffusion measurement can comprise the successive acquisition of image data that should be corrected for different diffusion weightings and diffusion directions, wherein an improved diffusion model can respectively be determined after acquisition of the image data. It is also possible to entirely forego a preceding adjustment measurement, such that the diffusion model is determined in the course of the actual diffusion measurement.

The output image data can be determined as a model parameter in the determination of the diffusion model on the basis of the acquired image data sets. The output image data can thus be obtained in the adaptation of the diffusion model to the image data sets with the least squares method as a model parameter. For example, for this the image data sets are acquired for the different diffusion directions given at least two different diffusion weightings.

However, it is likewise conceivable to acquire the output image data in an imaging MRT measurement without diffusion weighting. Both methods can likewise be applied in parallel to determine the output image data in order to achieve a check or an increase of the precision.

In one embodiment of the method, the method furthermore includes the implementation of at least one imaging MRT measurement with a predetermined diffusion weighting to acquire the image data to be corrected.

The method steps can be implemented automatically by a computer. A fast, automatic correction of the acquired image data is thus enabled without the necessity of a user interaction.

According to a further aspect of the present invention, a magnetic resonance system is provided that is designed to correct distortions in image data in a diffusion imaging. The magnetic resonance system has an acquisition unit that is designed to implement an imaging MRT measurement with a predeterminable diffusion weighting; a control unit that is designed to control the acquisition unit to acquire image data (which map a predetermined image segment) with a predetermined diffusion weighting; and a computer. The computer is designed to determine a diffusion model for the image segment; determine output image data for the image segment such that the output image data are essentially free of distortions caused by diffusion weighting; estimate reference image data for the predetermined diffusion weighting for the image segment based on the output image data and the diffusion model; compare the acquired image data with the reference image data; and correct the acquired image data based on the comparison.

Advantages similar to those described above can be achieved with the magnetic resonance system according to the invention. According to one embodiment, the magnetic resonance system is designed to implement one of the aforementioned methods.

The present invention also encompasses a non-transitory computer-readable storage medium encoded with programming instructions that, when the programming instructions are loaded into a computer or a computer system, cause the computer or computer system to implement the method described above, as well as all embodiments thereof.

DESCRIPTION OF THE PREFERRED EMBODIMENTS

Figure 1:
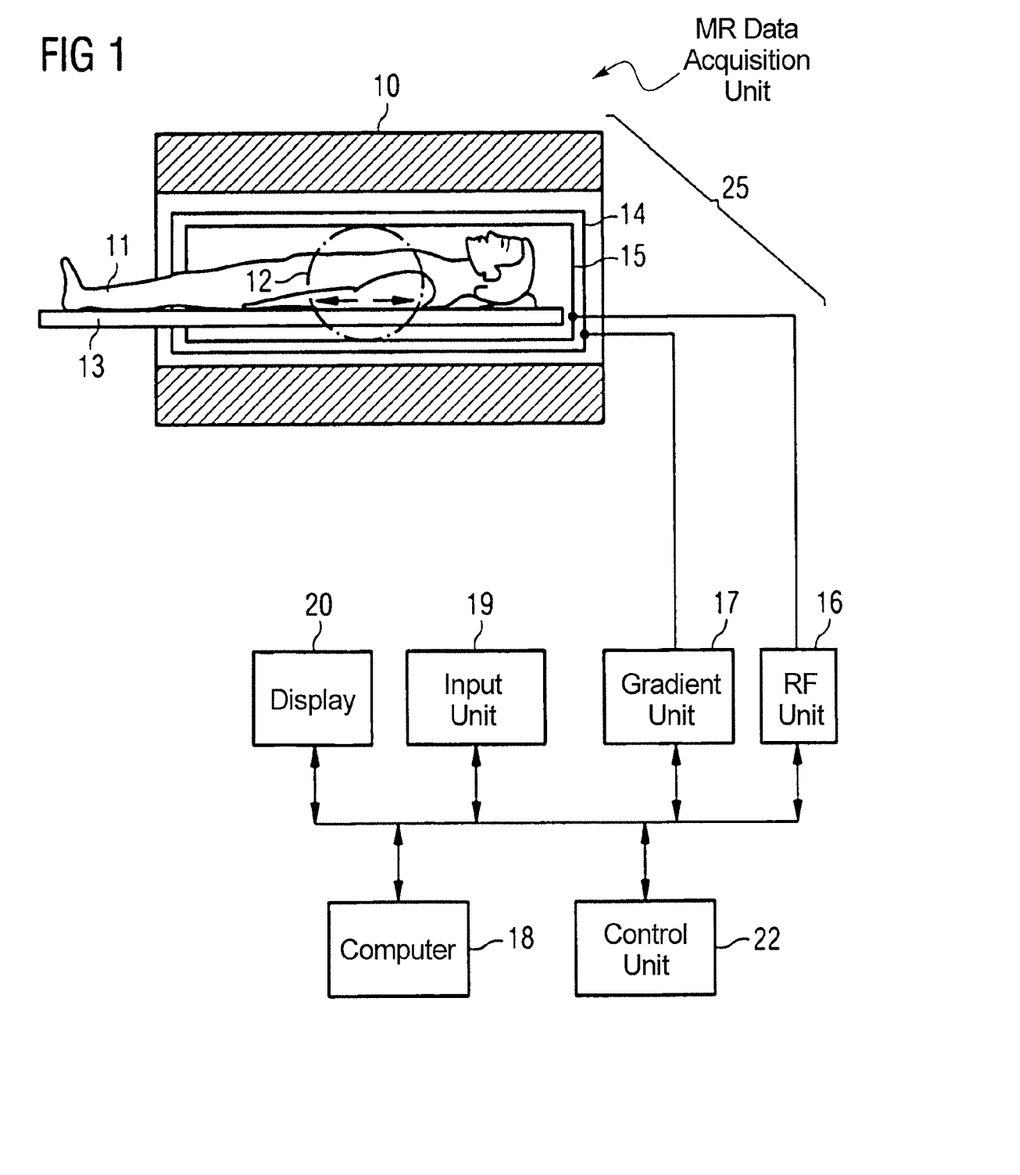
FIG. 1 schematically shows an embodiment of the magnetic resonance system according to the invention.

FIG. 1 schematically shows a magnetic resonance system which is configured to implement diffusion measurements, in particular to acquire diffusion-weighted image data. Such a magnetic resonance system has a magnet 10 to generate a polarization field 11; it can be displaced on a bed table 13 into the magnet 10, as is schematically indicated by the arrows. The MR system furthermore has a gradient system 14 to generate magnetic field gradients that are used for the imaging and spatial coding. Furthermore, diffusion coding gradients can be generated with the gradient system 15 for diffusion-weighted imaging. The strength and temporal switching of the diffusion gradients thereby significantly determines the diffusion weighting b, in contrast to which the direction in which the gradients are shifted (diffusion gradient direction g) determines the diffusion direction that is mapped in the image data. Diffusion imaging is sensitive to a diffusion of water molecules along this diffusion direction predetermined by the shifted gradients.

To excite the polarization resulting in the primary field, a radio-frequency coil arrangement 15 is provided that radiates a radio-frequency (RF) field into the examined person 11 in order to deflect the magnetization from the steady [equilibrium] state. For example, both excitation pulses—such as 90° sinc pulses—or rephasing pulses—for example 180° pulses—can be radiated by means of the RF coil arrangement 15. A gradient unit 17 is provided to control the magnetic field gradients and an RF unit 16 is provided to control the radiated RF pulses. Gradient system 14 and radio-frequency coil arrangement 15, as well as RF unit 16 and gradient unit 17, can together be designated as an MR data acquisition unit 25.

The control unit 22 centrally controls the magnetic resonance system, for example the implementation of a predetermined imaging MR sequence given predeterminable diffusion weighting and diffusion direction. A selection of the imaging sequence to be implemented can ensue with the input unit 19. Control information—for example imaging parameters—as well as reconstructed image data can be displayed on the display 20. Parameters for diffusion imaging—for example the b-values and diffusion directions for which the acquisition of image data should ensue—can also be selected via the input unit. Furthermore, the magnetic resonance system comprises a computer 18 that serves for the reconstruction of the image data from acquired MR signals as well as for the correction of distortions in such reconstructed image data (which correction is described in greater detail in the following).

The magnetic resonance system schematically shown in FIG. 1 can naturally comprise additional components that magnetic resonance systems conventionally possess. The general mode of operation of an MR system is known to those skilled in the art, such that a detailed description of the general components is not necessary.

Upon implementing a diffusion measurement with the magnetic resonance system to acquire diffusion-weighted image data, control unit 22 can initially instigate the implementation of an adjustment measurement in which a specific number (for example six) of image data sets are acquired with a predetermined diffusion weighting for different diffusion directions. From acquired MR signals the control unit 18 reconstructs the corresponding image data sets that map a segment of the examination region 12. Computer 18 furthermore determines a diffusion model that, for example, comprises a diffusion tensor for each image element of the imaged segment. Control unit 22 thereby controls the acquisition of the image data such that the condition $$\sum_{i=1}^{N} b_i \cdot g_i \approx 0 \quad (1)$$

is satisfied for the acquisition of a number N of image data sets. If the weighted diffusion gradient directions $g_i$ add up to a null vector, the eddy current-induced distortions in the image data sets of the adjustment measurement essentially cancel out in the determination of the diffusion model. The parameters b and g can be adjusted by the control unit 22 by predetermining the strength and the direction of the applied magnetic field gradients. Furthermore, computer 18 is designed to determine output image data for the image segment, wherein these can be obtained from the adaptation of the diffusion model to the acquired image data sets, or the acquisition of these can be initiated by control unit 22 by means of an MRT measurement without diffusion weighting. Computer 18 can implement a correction of the acquired image data by means of the determined output image data acquisition and the determined diffusion model. Control unit 22 instigates the acquisition of the image data in the diffusion measurement, wherein the desired diffusion weighting and direction can be predetermined by a user by means of input unit 19 or are predetermined by a measurement protocol. After acquisition of the MR signals and reconstruction of the image data, computer 18 determines corresponding reference image data for the acquired image data in that it applies the diffusion model for the predetermined diffusion weighting b and diffusion gradient direction g to the output image data. Since the underlying output image data are essentially distortion-free, the estimated reference image is also essentially distortion-free (in relation to the distortions caused by diffusion weighting). By using the diffusion model, the reference image data exhibit an image contrast that corresponds to that of the acquired image data. Control unit 18 is furthermore designed in order to implement a registration of the acquire image data with the reference image data as target images in order to determine the distortion parameters M, S and T of the transformation between these. Using the determined distortion parameters, computer 18 can subsequently implement a correction of the acquired image data for the distortions caused by the diffusion weighting.

Figure 2:
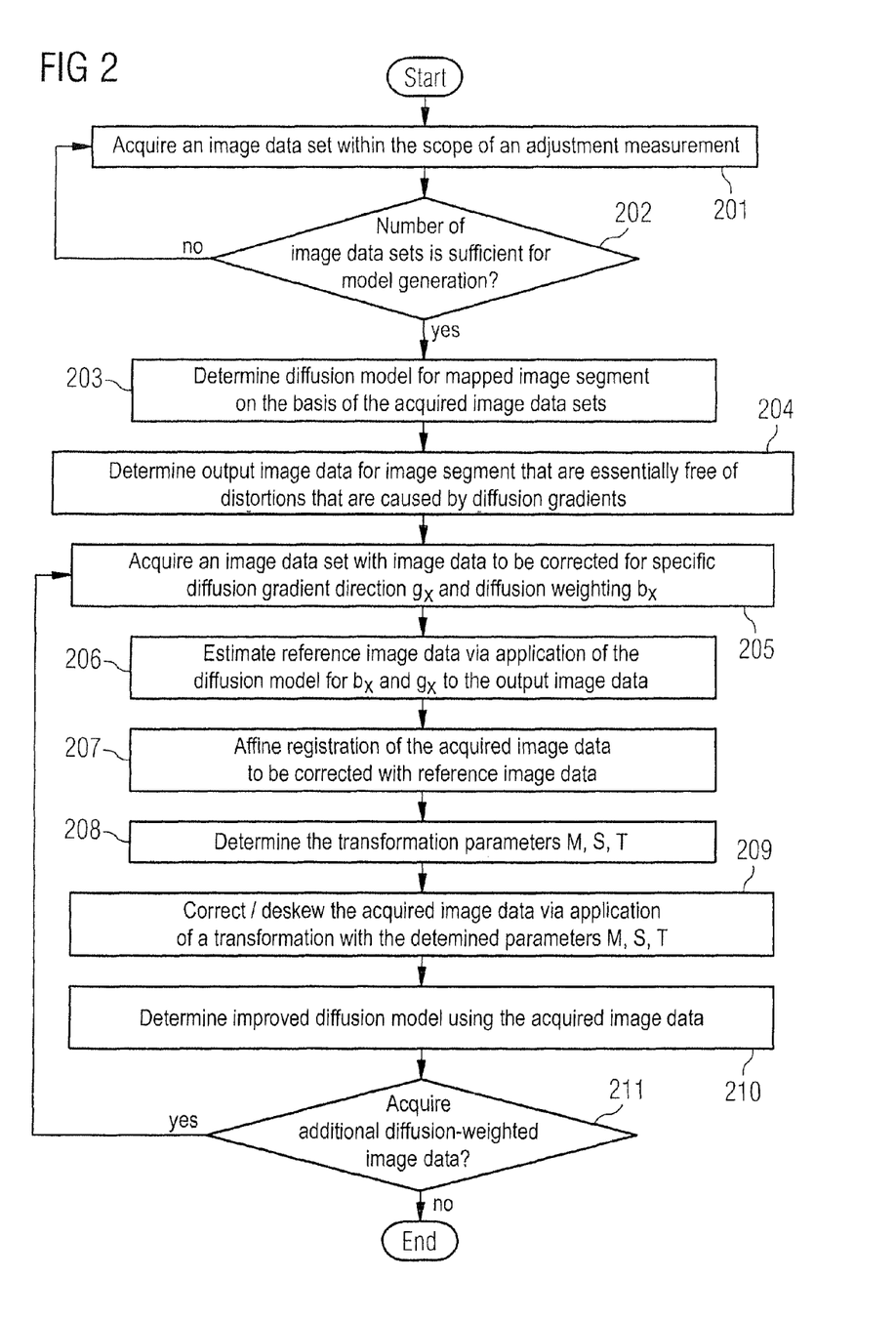
FIG. 2 is a flow chart of an embodiment of the method according to the invention.
Figure 3:
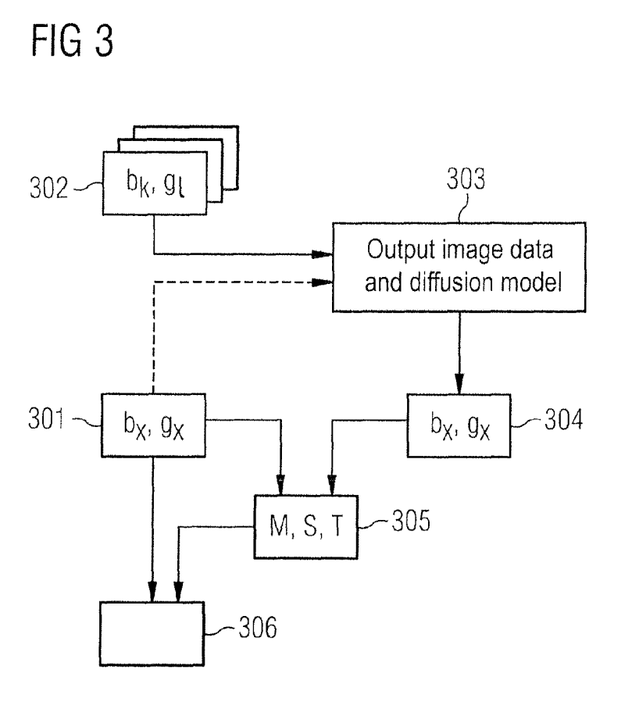
FIG. 3 schematically illustrates the determination of output image data and of a diffusion model, and of distortion correction parameters and of corrected image data according to one embodiment of the method according to the invention.

FIG. 2 shows a flow chart of an embodiment of the method according to the invention. The magnetic resonance system shown in FIG. 2 can be designed to implement the method. The acquisition of an image data set within the scope of an adjustment measurement ensues in a first step 201. The image data set is measured for a predetermined diffusion weighting or, respectively, weighting strength $b_k$ and a predetermined diffusion direction $g_1$. In decision step 202 it is checked whether the number of acquired image data sets is sufficient for the generation of a diffusion model. If this is not the case, an additional acquisition of image data sets ensues for additional diffusion directions $g_1$. The diffusion weighting $b_k$ can thereby be held constant or can likewise be varied. Given use of a diffusion tensor model, each diffusion tensor possesses six degrees of freedom, such that the acquisition of six image data sets is sufficient for the determination of this. However, more image data sets are advantageously acquired in order to enable a more precise determination of the model. In a preferred embodiment of the method, two image data sets with respectively opposite polarity of the shifted diffusion coding gradients are respectively acquired for six different diffusion directions. The satisfaction of Equation (1) (specified in the preceding) can thus be ensured in a simple manner so that distortions in the determination of the diffusion model are compensated. However, it should be clear that it is possible in principle to acquire an arbitrary number of image data sets for arbitrary diffusion directions and weightings as long as the requirements of the "white distribution" according to Equation (1) are present and as long as the number of measurements is sufficient to determine the degrees of freedom of the diffusion model that is used. Furthermore, it is advantageous that the adjustment measurements are not limited to low b-values or purely alternating measurements, as in conventional methods. The image data sets acquired for the parameters $b_k$ and $g_1$ are schematically illustrated in FIG. 3 and designated with the reference character 302.

In the next step 203 the diffusion model for the mapped image segment is determined on the basis of the acquired image data sets. The diffusion model describes the attenuation of the image intensity or, respectively, the MR signal depending on the diffusion direction and diffusion weighting, as well as the diffusion properties of the examined subject in the corresponding region. For example, a diffusion tensor model that associates a diffusion tensor of the 2nd order with every image element can be used as a diffusion model. However, more complex models can also be used such as kurtosis, QBall, HARDI (High Angular Resolution Diffusion Imaging), MultiTensor and others. It is only significant that the diffusion model can describe the change of the image intensities in the acquired image data sets with the change of the diffusion direction and weighting. For example, a simple diffusion model of the form $$S(b,g) = S_0 \cdot e^{-b g^T D g} \quad (2)$$

can be used that describes the attenuation of the MR signal intensity S depending on the diffusion weighting b, diffusion direction g and the diffusion tensor D, wherein $S_0$ represents the output signal intensity (from the output image data) without diffusion weighting. The at least six diffusion measurements with isotropically distributed diffusion directions g with the same diffusion weighting b and a b=0 (unweighted) measurement are used to estimate the diffusion tensor D. The parameters of the diffusion model—for example the components of the diffusion tensors—can be determined by adapting the model to the acquired image data sets, wherein the adaptation ensues with a least squares method.

Before the determination of the diffusion model, a selection of the image data sets that should be used for the model generation can also ensue. The measured image data sets can be examined for artifacts or rigid movements and—depending on the result of the examination—can be excluded from use for model determination, remeasured in Step 201 or corrected. Methods to increase the signal-to-noise ratio can also be applied to the acquired image data sets. If the diffusion model is still not complete in Step 203—for example because insufficient image information is present or the diffusion model shows deviations from the acquired image data sets that are too significant—the workflow can jump back to Step 201 and additional data sets can be acquired for model determination.

In Step 204 the determination of output image data that are essentially free of distortions that are caused by the diffusion gradients applied in the image acquisition ensues for the image segment. Both the image data acquired without diffusion weighting and image data determined in the adaptation of the diffusion model can thereby be used as output image data. In the adaptation of Equation (2) to the acquired image data sets, the parameter $S_0$ can be determined that essentially corresponds to an acquisition of magnetic resonance signals without diffusion weighting. By determining the parameter $S_0$ for the individual image data points, an image data set can be reconstructed for b=0. Both the image data acquired without diffusion weighting and the reconstructed $S_0$ image data are essentially free of distortion. The output image data and the diffusion model that are determined on the basis of the acquired image data sets 202 are labeled with the reference character 303 in FIG. 3. A reference image for every given (b, g) value pair which does not possess any distortions due to eddy currents can now be generated by means of the output image data and the diffusion model.

The acquisition of an image data set with image data to be corrected ensues in a next step 205 for a predetermined diffusion gradient direction $g_x$ and diffusion weighting bx. Depending on the application, the values $g_x$ and $b_x$ can thereby be arbitrarily adjusted. In particular given high b-values, significant distortions caused by diffusion occur, wherein the image data moreover exhibit a low signal-to-noise ratio due to the acquisition with high sensitivity. The acquired image data to be corrected are marked with the reference character 301 in FIG. 3.

After creation of the diffusion model, reference images for distortion correction can be generated for arbitrary diffusion weightings and directions. The estimation of reference image data ensues in Step 206 via application of the diffusion model for the acquisition parameters $b_x$ and $g_x$ to the output image data. Given use of the diffusion tensor model, Equation (2) is essentially evaluated for the given parameters $b_x$ and $g_x$ and the reference image is determined from the result. With this approach the reference image exhibits a significantly higher signal-to-noise ratio than the acquired image data, as is illustrated in the following in FIG. 7. The contrast ratio of the reference images is also essentially identical to that of the measured images. Given a comparison of the determined reference image data with the measured image data by means of an affine image registration, the consideration of contrast variations is now unnecessary (Step 207). The registration can accordingly be implemented with increased precision. In the image registration the measured image data are initially aligned on the reference image data in order to achieve an optimally good agreement between these. The transformation is subsequently sought that transforms the image data into one another. According to Step 208, the transformation parameters M, S and T are accordingly determined in the registration of the measured image data with the reference image data. The determination of the transformation parameters 305 is likewise illustrated in FIG. 3.

The deskewing or, respectively, correction of the acquired image data ensues in Step 209 via application of a transformation with the determined parameters M, S and T. The implementation of the distortion correction with reference image data specifically generated for the measured image data increases the precision of the correction in comparison to methods that are based on an extrapolation of weak distortions.

The precision of the method can be additionally increased via joint consideration of all diffusion directions and weightings and via physically motivated assumptions (linear superposition of the distortion effects of the individual gradient axes, linear increase of the development of the distortions with the gradient amplitude). In what is known as an inline concurrent measurement, in Step 210 an improved diffusion model can furthermore be determined on the basis of the acquired image data. The diffusion model can thus be continuously improved during the actual diffusion measurement. However, this method step is optional.

If additional diffusion-weighted image data are to be acquired in the decision step 211, the method branches back to Step 205 where the acquisition of an image data set ensues again for a parameter pair $g_x$ and $b_x$. If all image data sets were acquired for the diffusion measurement to be implemented, the method ends. Naturally, the method can comprise additional steps not explicitly shown in FIG. 2 that are typically executed in methods for diffusion-weighted imaging.

The determination of the corrected image data 306 via application of the transformation with the specific parameters 305 to the measured image data 301 is likewise illustrated in FIG. 3. FIG. 3 likewise shows that the measured image data 301 can be used to improve the diffusion model 303. It should be clear that a diffusion measurement can include the acquisition of a plurality of image data sets with image data 301 for different parameters $b_x$ and $g_x$.

Figure 4:
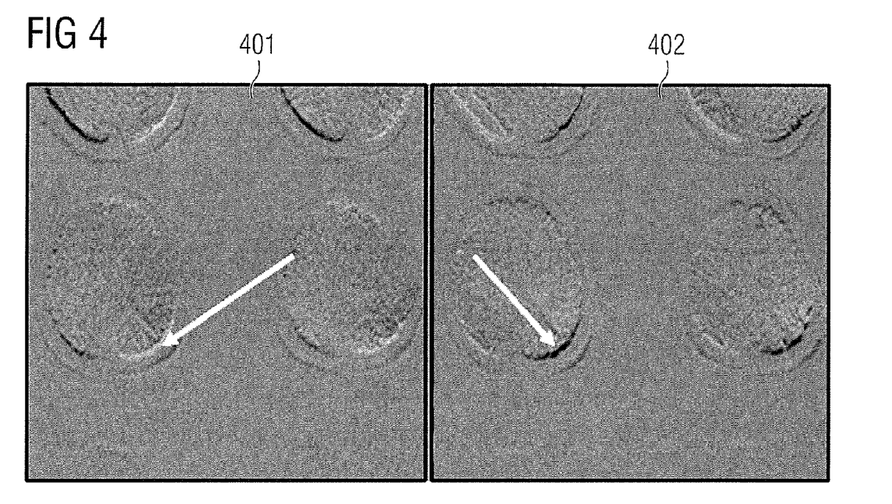
FIG. 4 illustrates the inversion of distortions given an inverted polarity of diffusion coding gradients, wherein difference images of reference image data and measured image data are shown.

Subsequent Figures illustrate image data that were obtained via application of the method. FIG. 4 shows difference images 401 and 402 between a respective reference image determined on the basis of the diffusion model and a measured image. The measured images were thereby acquired with inverted polarity of the diffusion coding gradients. The differences between the reference image and the respective measured image are correspondingly inverted in the difference image 402 in relation to the difference image

401. the diffusion model was thereby obtained by means of a tensor estimation according to the method described above. The arrows mark the differences due to eddy currents with inverted intensity in the difference images.

Figure 5:
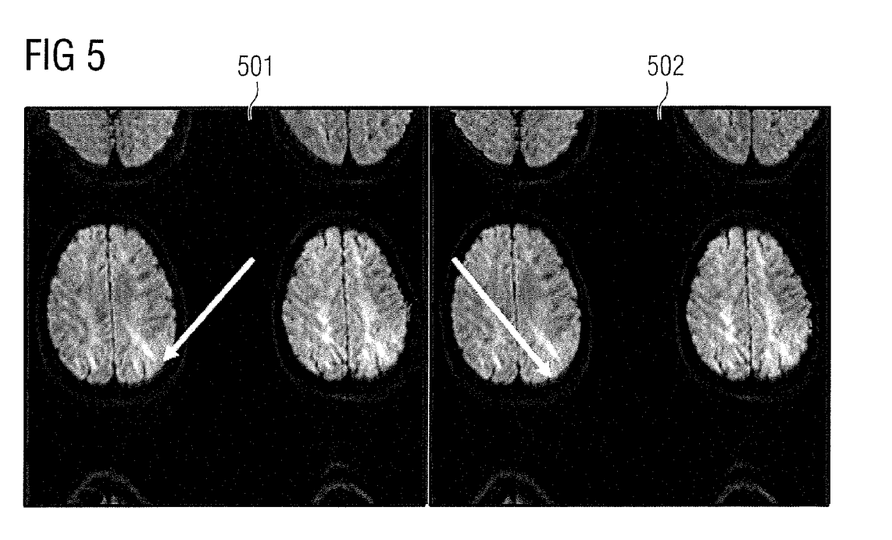
FIG. 5 illustrates reference image data that were determined using output image data and a diffusion model.

FIG. 5 shows the corresponding reference images 501 with positive polarity of the diffusion gradients and 502 with negative polarity of the diffusion gradients. The two images were determined for the value pair (b, g)=(1000, Direction 4). The corresponding positions marked by the arrows in the images do not show any distortions due to eddy currents. Such reference images can be generated for arbitrary value pairs on the basis of the output image data and the diffusion model.

Figure 6:
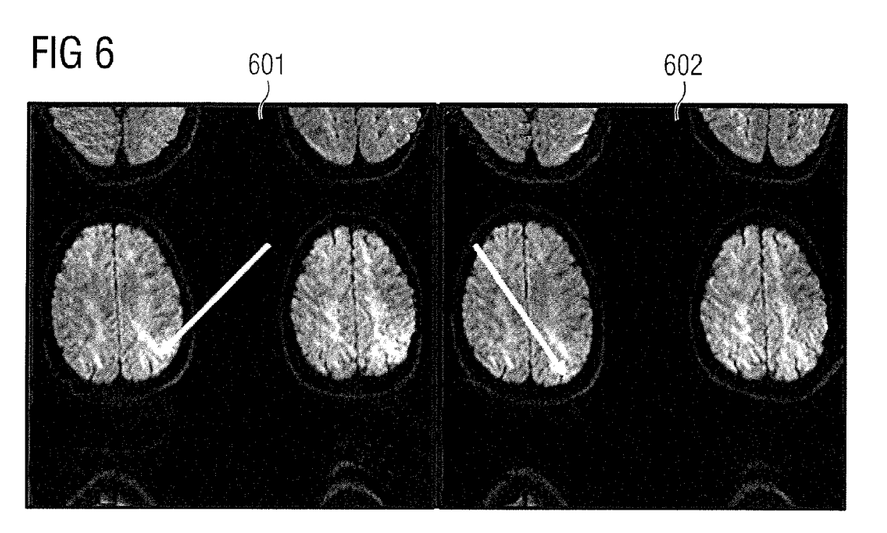
FIG. 6 illustrates distortions in acquired, diffusion-weighted image data that are caused by typical eddy current effects.

FIG. 6 shows the corresponding, measured diffusion images 601 and 602 that were acquired for the same value pair (b, g)=(1000, 4) with positive (601) and negative (602) polarity. The corresponding positions (marked with the arrows) in the diffusion-weighted images show the typical eddy current effects that can be caused by the shifting of the diffusion coding gradients. The reference images 501 and 502 shown in FIG. 5 can be used in the affine registration of the measured images 601 and 602 as target images to determine the parameters M, S and T.

Figure 7:
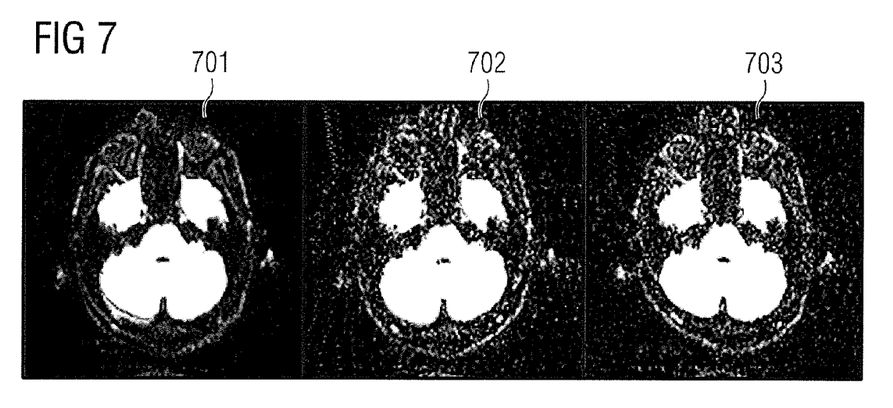
FIG. 7 illustrates the improvement of the signal-to-noise ratio in the determined reference images in comparison to image data acquired with the same diffusion weighting.

FIG. 7 illustrates the better signal-to-noise of the determined reference images in comparison to the measured images. In particular given a high diffusion weighting (large b-values), the determination of the transformation parameters is facilitated by the higher signal-to-noise ratio and the precision of the parameter determination is improved. Image 701 shows the estimated reference image, wherein images 702 and 703 show measured image data for the diffusion direction 4 with positive or, respectively, negative polarity. In the depiction the noise contribution for both the reference image 701 and the measured images 702 and 703 is shown increased by the same factor in order to more clearly illustrate the improvement of the signal-to-noise ratio. The distortion of the image data that depends on the diffusion gradient direction is clearly recognizable in images 702 and 703.

The features of the embodiments described in the preceding can naturally be combined. A number of modifications is also possible. For example, only a portion of the image data necessary to determine the diffusion model can be acquired during the adjustment measurement, in contrast to which the additional image data required for model determination are acquired in the course of the diffusion measurement.

In summary, an improved method for correction of distortions in image data in a diffusion-weighted imaging is provided with the present invention. A reference image which exhibits no distortions due to diffusion can thereby be determined based on the determined output image data and the determined diffusion model without additional measurements for each image acquired with a specific diffusion weighting and diffusion direction. A precise correction of the acquired image data is therefore possible. Disadvantages—such as a deviating contrast between acquired image data and reference image data, extrapolation errors and the necessity of the acquisition of additional image data for the correction—can be avoided with the method.

Although modifications and changes may be suggested by those skilled in the art, it is the intention of the inventor to embody within the patent warranted hereon all changes and modifications as reasonably and properly come within the scope of his contribution to the art.

We claim as our invention:

1. A method for correcting distortions in image data in diffusion imaging in magnetic resonance tomography, comprising the steps of:

acquiring image data with an imaging magnetic resonance tomography scan for a predetermined diffusion weighting, and image data mapping a predetermined image segment;

supplying said image data to a computerized processor, and in said computerized processor, determining a diffusion model for said image segment;

in said processor, determining output image data for said image segment that are substantially free of distortions caused by diffusion weighting associated said diffusion model;

estimating reference image data for said predetermined diffusion weighting for said image segment based on said output image data and said diffusion model;

in said processor, comparing the acquired image data with said reference image data to obtain a comparison result; and in said processor, using said comparison result to correct distortions in said acquired image data.

2. A method as claimed in claim 1 comprising comparing said acquired image data with said reference image data by determining a transformation, as said comparison result, between said acquired image data and the said reference image data, and correcting said acquired image data by applying said transformation to said acquired image data.

3. A method as claimed in claim 2 comprising determining said transformation by operating on said acquired image data with at least one transformation procedure selected from the group consisting of scaling, shearing, and shifting.

4. A method as claimed in claim 1 comprising acquiring said image data with said predetermined diffusion weighting embodying a predetermined diffusion gradient direction, and comprising estimating said reference image data for said predetermined diffusion gradient direction to give said reference image data and image contrast that is substantially the same as an image contrast of the acquired image data.

5. A method as claimed in claim 1 comprising acquiring said image data in a diffusion gradient direction, and comprising estimating said reference image data for said diffusion gradient direction.

6. A method as claimed in claim 1 wherein said image segment is comprised of a plurality of image elements, and comprising employing, as said diffusion model, a diffusion model that comprises a diffusion tensor for each of said image elements in said image segment.

7. A method as claimed in claim 1 comprising employing, as said diffusion model, a diffusion model selected from the group consisting of a HARDI model, a kurtosis model, a QBall model, and a multi-tensor model.

8. A method as claimed in claim 1 comprising employing, as said diffusion model, a diffusion model that describes a change in intensity of image data with diffusion weighting and diffusion gradient direction, and comprising estimating said reference image data by applying said diffusion model for said diffusion weighting and said diffusion gradient direction to said output image data.

9. A method as claimed in claim 1 comprising determining said output image data for said image segment to correspond to image data acquired in a magnetic resonance tomography scan that was not diffusion weighted.

10. A method as claimed in claim 1 comprising acquiring said image data in multiple image data sets for respectively different diffusion gradient directions, with the same or different diffusion weightings, and determining said diffusion model in said computerized processor from said multiple image data sets.

11. A method as claimed in claim 10 comprising determining said diffusion model using a method of least squares.

12. A method as claimed in claim 11 comprising selecting respective diffusion gradient directions and diffusion weighting for acquiring said multiple image data sets for determining said diffusion model, to cause a sum of the diffusion directions, weighted with the respective diffusion weightings, to substantially produce a null vector.

13. A method as claimed in claim 11 comprising acquiring at least six image data sets for different diffusion gradient directions and six image data sets with respectively opposite diffusion gradient directions, with the same respective diffusion weightings.

14. A method as claimed in claim 11 comprising acquiring one of said image data sets without diffusion weighting.

15. A method as claimed in claim 11 comprising acquiring at least some of said multiple image data sets with an adjustment measurement implemented before acquisition of an image data set that is to be corrected.

16. A method as claimed in claim 11 comprising, in said processor, analyzing the multiple acquired image data sets for image interference and, for any of said multiple image data sets that are determined to exhibit image interference, initiating a response in said processor selected from the group consisting of correcting said image interference, and excluding, in determining said diffusion model, use of any of said image data sets that exhibit image interference.

17. A method as claimed in claim 11 comprising determining said output image data as a model parameter in determining said diffusion model, based on the multiple acquired image data sets.

18. A method as claimed in claim 1 comprising acquiring said output image data in an imaging magnetic resonance tomography scan without diffusion weighting.

19. A method as claimed in claim 1 comprising acquiring said image data to be corrected by executing at least one imaging magnetic resonance tomography scan with a predetermined diffusion weighting.

20. A method as claimed in claim 1 comprising determining said diffusion model dependent on the acquired image data to be corrected.

21. A magnetic resonance system, comprising:
a magnetic resonance data acquisition unit configured to acquire image data in an imaging magnetic resonance tomography scan for a predetermined diffusion weighting, said image data mapping a predetermined image segment;
a computerized processor supplied with said image data, said processor being configured to determine a diffusion model for said image segment;
said processor being configured to determine output image data for said image segment that are substantially free of distortions caused by diffusion weighting associated said diffusion model;
said processor being configured to estimate reference image data for said predetermined diffusion weighting for said image segment based on said output image data and said diffusion model;
said processor being configured to compare the acquired image data with said reference image data to obtain a comparison result; and
said processor being configured to use said comparison result to correct distortions in said acquired image data.

22. A non-transitory computer-readable medium encoded with programming instructions, said programming instructions, when loaded into a computerized system supplied with image data acquired in an imaging magnetic resonance tomography scan for a predetermined diffusion weighting, that map a predetermined image segment, causing said computer system to:
determine a diffusion model for said image segment;
determine output image data for said image segment that are substantially free of distortions caused by diffusion weighting associated said diffusion model;
estimate reference image data for said predetermined diffusion weighting for said image segment based on said output image data and said diffusion model;
compare the acquired image data with said reference image data to obtain a comparison result; and
use said comparison result to correct distortions in said acquired image data.

* * * * *